United States Patent [19]

Sullivan

[11] Patent Number: 5,234,162
[45] Date of Patent: * Aug. 10, 1993

[54] AIR FRESHENER DEVICE CARTRIDGE

[75] Inventor: William E. Sullivan, Blythewood, S.C.

[73] Assignee: Ecolab Inc., St. Paul, Minn.

[*] Notice: The portion of the term of this patent subsequent to Sep. 24, 2008 has been disclaimed.

[21] Appl. No.: 762,156

[22] Filed: Nov. 26, 1991

Related U.S. Application Data

[62] Division of Ser. No. 406,724, Sep. 13, 1989, abandoned.

[51] Int. Cl.$^5$ .................................................. A61L 9/04
[52] U.S. Cl. ..................................... 239/56; 221/66; 239/51.5; 239/55; 239/57; 239/58; 422/5; 422/122
[58] Field of Search ........................ 422/5, 120, 122; 239/51.5, 53–60; 221/66

[56] References Cited

U.S. PATENT DOCUMENTS

| | | | |
|---|---|---|---|
| 1,080,716 | 12/1913 | Rand, Jr. | 239/55 |
| 1,496,326 | 6/1924 | Schulte | 239/57 |
| 1,972,368 | 9/1934 | Alex | 239/55 X |
| 2,297,984 | 10/1934 | Reller | 132/315 |
| 2,585,339 | 2/1952 | Miller | 422/124 |
| 2,603,468 | 7/1952 | Sutton | 261/104 |
| 2,614,820 | 10/1952 | Boydjieff | 261/26 |
| 2,615,563 | 10/1952 | Sundberg et al. | 206/541 |
| 2,629,149 | 2/1953 | Yaffe | 422/124 |
| 3,415,361 | 12/1968 | Adams | 206/221 |
| 3,575,346 | 4/1971 | Roth | 239/57 |
| 3,711,023 | 1/1973 | Smith | 239/55 |
| 3,807,082 | 4/1974 | Hautmann et al. | 424/78 X |
| 3,908,905 | 9/1975 | Von Philipp et al. | 239/55 |
| 3,990,848 | 11/1976 | Corris | 422/49 |
| 3,993,444 | 11/1976 | Brown | 422/116 |
| 4,035,451 | 7/1977 | Tringali | 261/101 |
| 4,059,422 | 11/1977 | Steiner | 239/55 X |
| 4,094,119 | 6/1978 | Sullivan | 53/400 |
| 4,229,415 | 10/1980 | Bryson | 422/109 |
| 4,271,092 | 6/1981 | Sullivan et al. | 261/30 |
| 4,276,236 | 6/1981 | Sullivan et al. | 261/30 |
| 4,301,095 | 11/1981 | Mettler et al. | 261/30 |
| 4,352,457 | 10/1982 | Weick | 239/57 X |
| 4,415,092 | 11/1983 | Boyer | 211/60 R X |
| 4,432,938 | 2/1984 | Meetze, Jr. | 422/49 |
| 4,477,414 | 10/1984 | Muramoto et al. | 422/125 |
| 4,523,870 | 6/1985 | Spector | 239/57 X |
| 4,529,125 | 7/1985 | Sullivan | 239/56 |
| 4,695,434 | 9/1987 | Spector | 422/116 |
| 4,761,008 | 8/1988 | Huggins | 273/148 R |
| 4,840,770 | 6/1989 | Walz et al. | 422/49 |
| 4,857,240 | 8/1989 | Kearnes et al. | 261/26 |
| 4,911,296 | 3/1990 | Hart, Jr. | 220/22 X |
| 5,023,020 | 6/1991 | Machida et al. | 422/124 X |
| 5,050,798 | 9/1991 | Sullivan | 239/58 |
| 5,064,624 | 11/1991 | King | 422/123 |

Primary Examiner—Robert J. Warden
Assistant Examiner—Amelia Santiago
Attorney, Agent, or Firm—Merchant, Gould, Smith, Edell, Welter & Schmidt

[57] ABSTRACT

An air freshener device (10) having a cartridge (14) and a cartridge housing (16) is disclosed. The housing (16) has a sealed first cavity (18) and a sealed second cavity (20) having a first fragrance (22) and a second fragrance (24), respectively. First and second cavities (18) and (20) have first and second opening (34) and (54) respectively. The device (10) includes a housing (12) having air passage openings (70), (76), (78), a fan (82) and power means (80) and also supports cartridge (14). When the power means (80) powers the fan (82) the air passage openings (70), (76) and (78) receive air which moves from the second (76) to the third (78) air passage opening and from the first air passage opening (70) across the cartridge (14) picking up the fragrances (22) and (24), resulting in an air-fragrance mixture which is drawn into an unobstructed air flow between the second and third air passage openings (76) and (78) and exits the third air passage opening (78), thereby allowing dispersion of the fragrance (22) and (24).

11 Claims, 5 Drawing Sheets

AIR FRESHENER DEVICE CARTRIDGE

This is a division of application Ser. No. 07/406,724 filed Sep. 13, 1989, which was abandoned upon the filing hereof.

BACKGROUND OF THE INVENTION

1. Field of the Invention

This invention relates generally to air freshener devices and cartridges. More particularly, this invention relates to air freshener devices having an evaporation controlled fragrance cartridge which has means for controlling the evaporation of at least two fragrances of different volatilities where the air flow to the cartridge is not obstructed.

2. Description of the Prior Art

Air freshener devices which utilize a fan typically direct air flow at the fragrance container. This construction causes the velocity of the air to decrease as it collides with the fragrance container. Therefore, the air flow is weak and thus, the fragrance output of the air freshener apparatus is deficient.

For example, U.S. Pat. No. 4,432,938, issued Feb. 21, 1984 to Murray O. Meetze, Jr., discloses an apparatus for creating a flow of air past a product capable of being vaporized. This apparatus is specifically designed for use with a device that holds the product for release through a permeable membrane. The apparatus includes components for creating a flow of air past or against the device to distribute the volatile product into the environment.

U.S. Pat. No. 4,301,095, issued Nov. 17, 1981 to Leo L. Mettler et al, discloses an air freshener dispenser. The air freshener dispenser disclosed shows an air flow pattern where air enters the housing in all directions and impinges upon a disk which contains the volatile fragrance. The volatilization takes place as the air impinges upon the bottom surface of the pad. The volatilized liquid escapes in a path that is 360° or a total circle at the point of air entry.

These devices direct air flow at the fragrance container. Therefore, the velocity of the air is decreased as it collides with the fragrance container and fragrance flow is impeded.

The present invention utilizes a device where the air flow is not obstructed. Fragrance vapor is drawn into the air stream by the low pressure created by the action of the fan blade. Therefore, the air-fragrance mixture which exits the device enters the environment at a greater velocity thereby aiding in the dispersion of the mixture.

Some types of air fresheners are designed to disperse a combined fragrance which includes fragrances of high and low volatility. The result of the typical design is that the evaporation of the fragrance of high volatility is much greater the first few days of exposure and thereafter evaporation rapidly falls off. This results in a short lived period when the combined fragrances are disseminated at an optimum level. Therefore, it is desirable to control evaporation of the fragrance.

One example where the evaporation of the fragrance is controlled to allow reproduction of a desired odor is U.S. Pat. No. 3,711,023, issued Jan. 16, 1973 to Dean E. Smith. An air conditioning system is disclosed which releases the evaporated volatile substances into the air to produce an odor. The individual compartments from which the odor is to be formed are stored in individual receptacles and the amount of individual components to be released are controllable. The mixing of various components may be controlled by varying the width of the passage way to vary the proportions of the fragrances being mixed. However, the system is not designed to obtain the even rate of evaporation of fragrances of different volatilities.

U.S. Pat. No. 4,477,414, issued Oct. 16, 1984 to Takayoshi Muramoto et al, discloses an apparatus for evaporating a solution of varying volatility (the solution contains ingredients of high, middle, and a low notes). A certain amount of the volatile liquid is allowed to be evaporated at one time. An evaporative container is used which comprises a container for holding the solution and a water absorbing impregnation element that is fitted to the head of the container and which uses the mechanism of a siphon to supply liquid to be evaporated. The use of a controlled dispenser allows the remaining solution to retain the original mixture of notes. This patent also includes a device wherein the amount of evaporation of the solution absorbed to be released can be controlled by a rotating lid. However, this device does not utilize the volatilities of the fragrances by effectively controlling evaporation through separate cavities.

The present invention addresses the problems associated with the prior art devices and provides an air freshener device that controls evaporation of the fragrances and provides an unobstructed air-fragrance flow out of the apparatus.

SUMMARY OF THE INVENTION

The present invention provides an air freshener device having an evaporation controlled fragrance cartridge which controls the evaporation of at least two fragrances of different volatilities where the air flow to the cartridge is not obstructed. The cartridge includes a housing having a sealed first cavity and a sealed second cavity. A first fragrance is located within the first cavity and a second fragrance is located within the second cavity where each of the fragrances has a volatility. The first cavity has a first opening where the opening has a removable cover and the second cavity has a second opening having a removable cover. When the cover is removed, the fragrances of first and second volatilities independently exit their respective cavities.

The air freshening device of the present invention also provides for a cartridge having a fragrance where a housing having a cavity holds the cartridge. The housing includes a cover member having a top, a bottom, a first side and a second side; a base member connected to the cover member and adapted and configured to be mounted on a surface; a first air passage opening proximate the second side of the cover member; a second air passage opening proximate the top of the cover member; and a third air passage opening proximate the bottom of the cover member and axially aligned with the second air passage opening. A fan is axially aligned between the second and third air passage opening and is cooperatively connected to the housing. A power means is connected to the housing where the power means is operatively connected to and adapted to power the fan. When the power means powers the fan, the air passage openings receive air which moves from the second to the third air passage openings and from the first air passage opening across the cartridge picking up the fragrance resulting in an air-fragrance mixture which is drawn into the unobstructed air flow between the second and third air passage opening and exits the third air passage opening thereby allowing dispersion of the fragrance.

Yet another aspect of the present invention includes a cartridge for an air freshener device having a housing where the housing has a sealed first cavity and a sealed second cavity. A first fragrance is located within a first cavity having a first volatility and a second fragrance is located within the second cavity having a second volatility. The second cavity contains a greater volume of fragrance than the first cavity where the first fragrance has a first volatility lower than the second volatility of the second fragrance. The first cavity has a first opening having a removable cover and the second cavity has a second opening having a removable cover. The first cavity has a generally larger opening than the second opening allowing greater exposure of the fragrance of lower volatility and less exposure of the fragrance of higher volatility. Therefore, when the removable cover is removed, the fragrance within the first and second cavities may independently exit their respective cavities thereby equalizing the rate of the evaporation of the fragrances. The rates of evaporation of the first and second fragrances are controlled, thereby causing the fragrances to expire at approximately the same time. The housing of the present invention may further form a single integral unit containing the first and second fragrances so that when the cover is removed and the unit is inserted into the air freshener device, the unit allows independent exiting of the first and second fragrances.

DESCRIPTION OF THE PREFERRED EMBODIMENT

Referring to the drawings, wherein like numbers represent like parts throughout the several views, there is generally disclosed at 10 an air freshener device. The apparatus includes a housing 12 and a cartridge 14. The cartridge 14 includes a cartridge housing 16.

Figure 2:
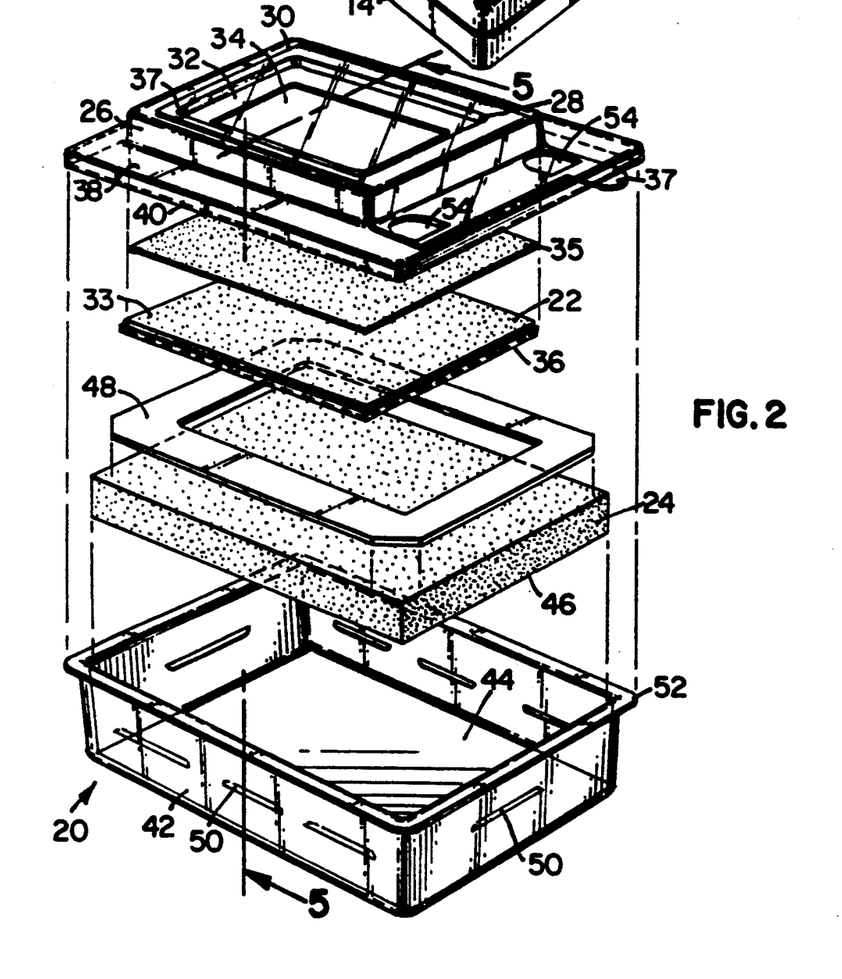
FIG. 2 is an exploded perspective view of the fragrance cartridge of the present invention.
Figure 5:
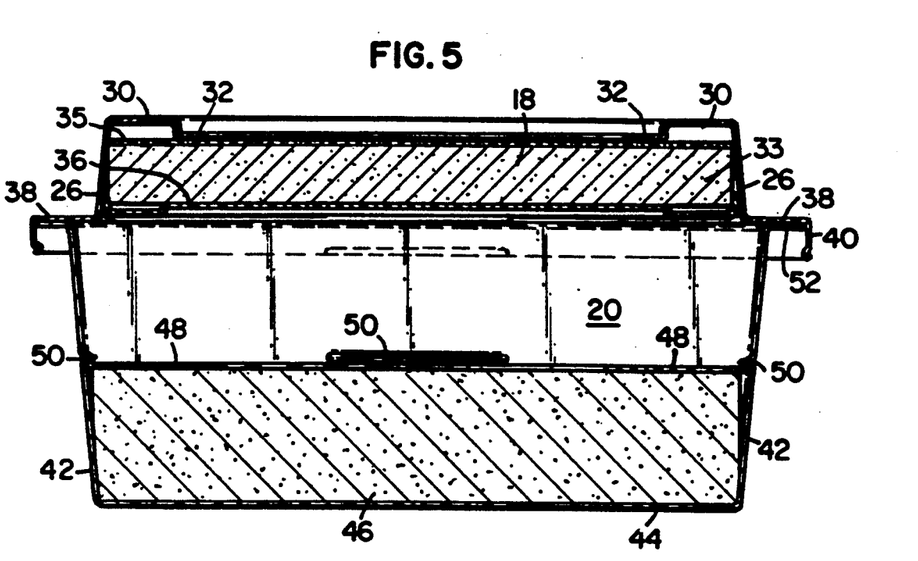
FIG. 5 is a cross sectional view of the fragrance cartridge of FIG. 2 taken along the line 5—5.

Referring to FIGS. 2 and 5, the cartridge housing 16 includes separately sealed first and second cavities 18 and 20. First cavity 18 contains first fragrance 22 having a first volatility. Second cavity 20 contains a second fragrance 24 having a second volatility. The first volatility is lower than the second volatility. The first cavity 18 contains a slow evaporating fragrance or base notes while the second cavity 20 contains a fast evaporating fragrance or top notes. Separately sealing the cavities 18 and 20 prevents mixing of the first fragrance 22 and the second fragrance 24 while in their respective cavities 18 and 20. The cartridge housing 16 is made of a barrier plastic in the preferred embodiment known as Barrex. The barrier plastic does not allow permeation of the fragrances from the cartridge 16 until the user desires to use the cartridge 16.

The first cavity 18 is formed by a continuous outer wall 26, continuous inner wall 28, top wall 30, and wall 32. Continuous outer wall 26 provides the outside boundary for the first cavity 18. Continuous outer wall 26 and continuous inner wall 28 are generally parallel to each other and both are generally perpendicular to top wall 30 and wall 32. Top wall 30 and wall 32 are connected by inner wall 28. These walls 26, 28, 30, and 32 are formed as a single integral unit or first cavity 18. First fragrance 22 is contained in a pad 33 in the preferred embodiment. A diffuser 35 is placed on top of pad 33 to maintain the position, surface, and placement of pad 33, as well as, to act as a diffuser. Pad 33 is made of a non-woven polyester in the preferred embodiment, although it should be understood that any other suitable material may be utilized. The fragrance from pad 33 wicks into diffuser 35 and evaporates from it. The diffuser 35 is made of spun bonded polyester in the preferred embodiment.

Wall 32 is shown with a selectable opening 34 in FIG. 2. The opening 34 is generally rectangular in the preferred embodiment and approximately measures 2⅛ inches by 2⅜ inches. The opening 34 is necessary to allow the first fragrance 22 to escape the cartridge 12. The end user will remove a cover 37 which is sized and configured to fit within or cover the opening 34 and connected to first cavity 18 by an adhesive to allow the first fragrance 22 to escape the sealed first cavity 18.

First cavity 18 is separately sealed from second cavity 20 by membrane 36. A lid 38 generally perpendicular to and connected to outer wall 26 in conjunction with membrane 36 seals the first cavity 18 from second cavity 20. A continuous first lip 40 which is generally perpendicular to and connected to lid 38 aids in separately sealing the cavities 18 and 20 which will be discussed in further detail later in this description. Membrane 36, lid 38 and first lip 40 form a single integral unit with first cavity 18. Membrane 36 is a barrier film and is made of a PET film in the preferred embodiment.

Second cavity 20 is formed by a continuous first wall 42 connected to a bottom wall 44. The first wall 42 forms the outside boundary for second cavity 20. The bottom wall 44 is generally perpendicular to the first wall 42 and the connection of these walls 42 and 44 forms the cavity 20. First wall 42 and bottom wall 44 are formed as a single unit or second cavity 20.

The second fragrance 24 is placed in pad 46 in the preferred embodiment and is located in the second cavity 20. The pad 46 is a non-woven polyester in the preferred embodiment. Retainer 48 is placed on the fragrance 24 and pad 46 to hold them in place. The retainer 48 generally forms a ring proximate the continuous first wall 42. The retainer 48 fits under and is kept in place by protrusions 50 in the first wall 42. The retainer 48 is constructed of PET film in the preferred embodiment.

A continuous second lip 52 is formed integrally with the first continuous wall 42 to aid in separately sealing the cavities 18 and 20. First lip 40 is generally formed to mate with second lip 52 to form the cartridge housing 16 which comprises first cavity 18 and second cavity 20. First lip 40 of the first cavity 18 is placed over second lip 52 to form a seal between the cavities 18 and 20. Selectible second openings 54 in the lid 38 provide a means for the second fragrance 24 to escape into the environment. The openings 54 are generally circular in the preferred embodiment and have a diameter of approximately ⅛ inch. The end user will remove cover 37 from the openings 54 to allow the second fragrance 24 to escape the sealed second cavity 20.

As previously discussed, the wall 32 has a selectible opening 34 aligned with cavity 18 while lid 38 has selectible second openings 54 aligned with second cavity 20 thereby providing a means for the fragrances 22 and 24 to exit their respective cavities 18 and 20. The openings 34 and 54 are covered by a removable cover 37. Cover 37 is utilized to retain the fragrances 22 and 24 until the end user removes the cover 37 for use. The removable cover 37 is sized and configured to cover the openings 34 and 54. In the preferred embodiment, the removable cover 37 must be removed by the end user in order for the fragrances 22 and 24 to escape their respective cavities 18 and 20. The removable cover 37 is peeled off of the cartridge housing 16 where it is attached by an adhesive, thereby exposing the openings 34 and 54. Therefore, when the cover 37 is removed, the fragrances 22 and 24 are free to independently exit their respective cavities 18 and 20. In the preferred embodiment, the cover 37 is a barrier plastic which is heat sealed to the cartridge 14. It should be understood that any other size, configuration or material of cover 37, including separate covers for each opening, may be utilized.

The use of a larger volume of fast evaporating top notes in the second cavity 20 and a smaller volume of slow evaporating base notes in the first cavity 18 allows equalization of the time periods for which the evaporation is optimal. In the preferred embodiment, the slow evaporating base notes have a larger opening 34 allowing for greater evaporation while the top notes have smaller openings 54 allowing slower evaporation. This control of evaporation allows for an air freshener with superior performance.

Figure 6:
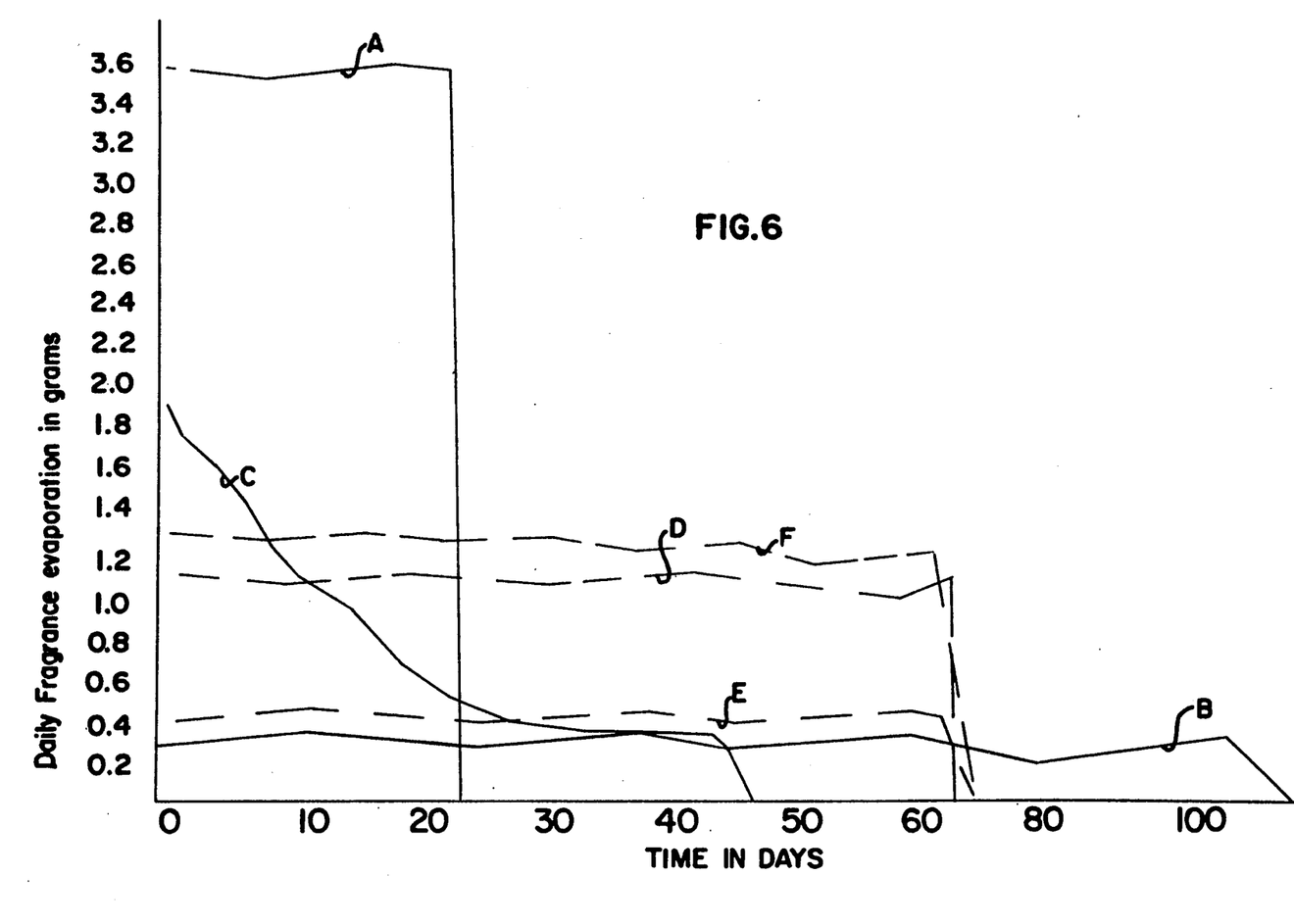
FIG. 6 is a graph of evaporation of fragrance versus time.

As an example, FIG. 6 shows the daily fragrance evaporation in grams versus time in days. Evaporation of the fragrances was measured daily. Fifty percent top notes and fifty percent base notes of cherry fragrance were used to achieve the results in FIG. 6. Cherry fragrance has a vast difference in volatility in top notes and base notes. As shown by line A, the top notes evaporated at a rapid rate, with approximately 3.5 to 3.6 grams evaporating per day. The cherry base notes evaporated quite slowly with an average of approximately 0.2 to 0.4 grams per day over 100 days, as shown by line B, whereas, the top notes evaporated in just over 20 days. Line C demonstrates the poor performance of 50% cherry top notes and 50% cherry base notes as used for a fragrance mixture. Rapid fall off of fragrance output demonstrates the need for evaporation control of the fragrances of high and low volatility.

FIG. 6 also demonstrates an example of the output of the present invention. A large evaporation surface is used for a small volume of expensive base notes while a small evaporation surface is used for a large volume of inexpensive top notes. The fragrances utilized were cherry top notes and cherry base notes. The large volume of cherry top notes escape through the small openings 54. This creates a change in evaporation of the top notes shown by the dashed line D. A small volume of expensive base notes reduces waste when utilized with a large evaporation surface. The daily fragrance evaporation of the base notes is shown by the dashed line E. The present invention reaches a generally level fragrance output by the controlled use of the top and base notes as shown by the dashed line F.

Figure 7:
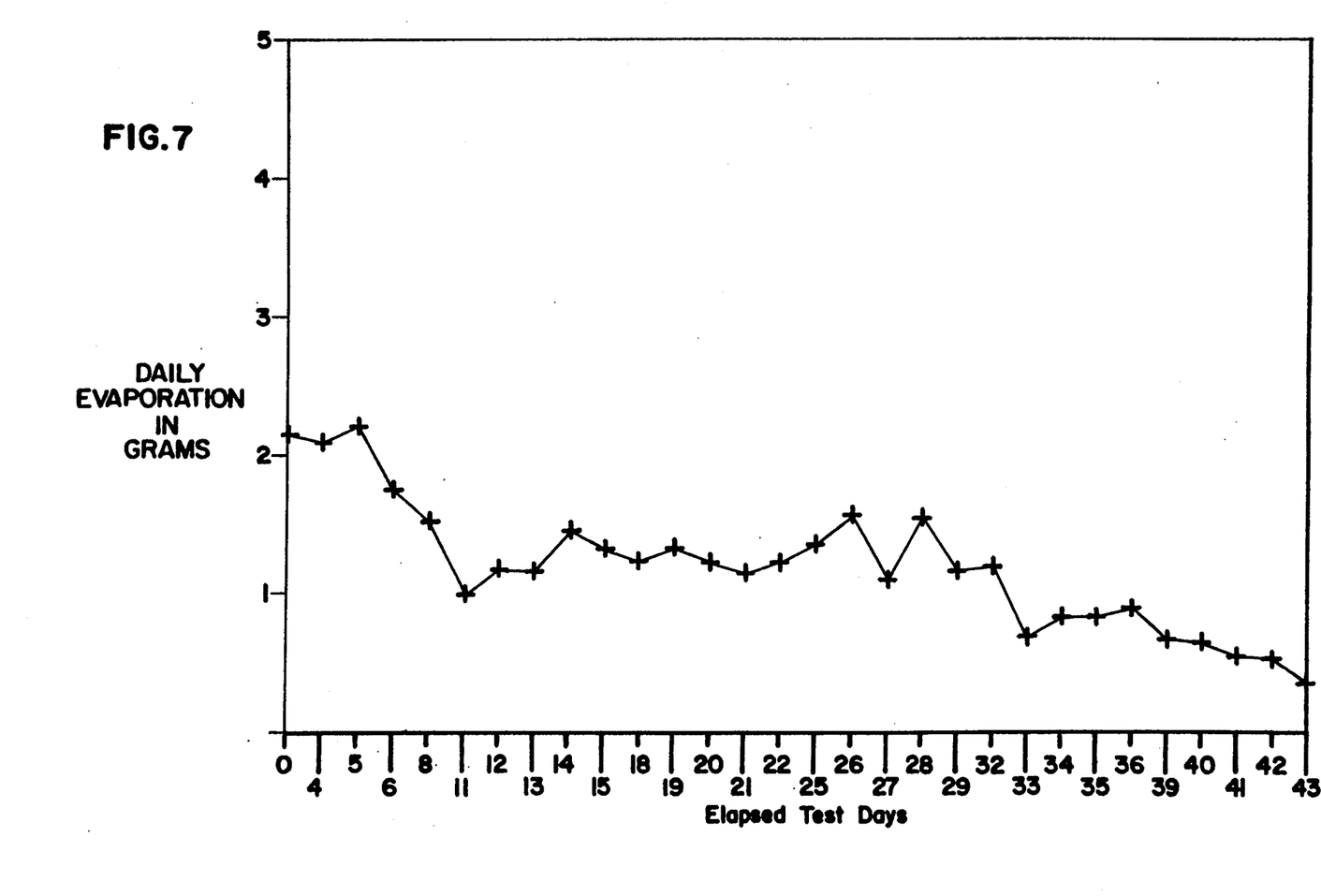
FIG. 7 is a graph of evaporation of fragrance versus time for the present invention.

Referring now to FIG. 7, results of a daily evaporation test for the present invention are shown. Fifty grams of cherry top notes were placed in the second cavity 20 and fifteen grams of cherry base notes were placed in first cavity 18. The fifty grams of cherry top notes included 50 grams of benzaldehyde and the fifteen grams of cherry base notes included 7.5 grams of pipernol and 7.5 grams of propylene G. The daily evaporation of the fragrances 22 and 24 were measured by weight. The cartridge 14 was placed in the housing 12 and the device was operated in the standard manner discussed later in this description. The results of this test are shown in FIG. 7. The controlled daily evaporation results in an air freshener having a daily evaporation of approximately 1.2-1.5 grams per day for a large majority of the test period. This controlled evaporation provides a device which provides the user with a longer lasting, constant fragrance output.

The configuration and the number of openings 34, 54 of each cavity 18, 20 is governed by the volatilities of the two fragrances 22, 24, the volumes of the two fragrances 22, 24, and the desired results. The openings 34, 54 are tailored to various fragrances. Different results can be reached with different combinations. For example, using a larger volume of base notes and a smaller volume of high notes will result in different rates of evaporation depending on the area exposed by the openings 34, 54. A greater number of openings in the base note cavity will produce a different result than if the high note cavity had a greater number of openings. Further, different fragrances may permit a smaller volume of fast evaporating top notes in the second cavity 20 and a larger volume of slow evaporating base notes in the first cavity 18 to achieve equalization of the time periods for which the evaporation is optimal.

The volatilities of top notes and base notes may be significantly different. For example, the volatility of Benzaldhyde (1100 microns at 25° C.) compared to the volatility of Ethyl Vanallin (0.15 microns at 25° C.) has a volatility ratio of over 7000 to 1. The following table provides further examples of volatilities of top notes and base notes.

|  | Fragrance Ingredient | Vapor Pressure in Microns at 25° Centigrade |
| --- | --- | --- |
| Top Notes | Benzaldhyde | 1100 |
|  | Spearmint oil | 250 |
|  | Limonene | 950 |
|  | Pinenedle oil Siberian | 580 |
|  | Methyl Salicylate | 118 |
| Base Notes | Citral | 58 |
|  | Carvone | 95 |
|  | Ethyl Vanallin | 0.15 |
|  | Emp Glicidate | 3 |

Figure 1:
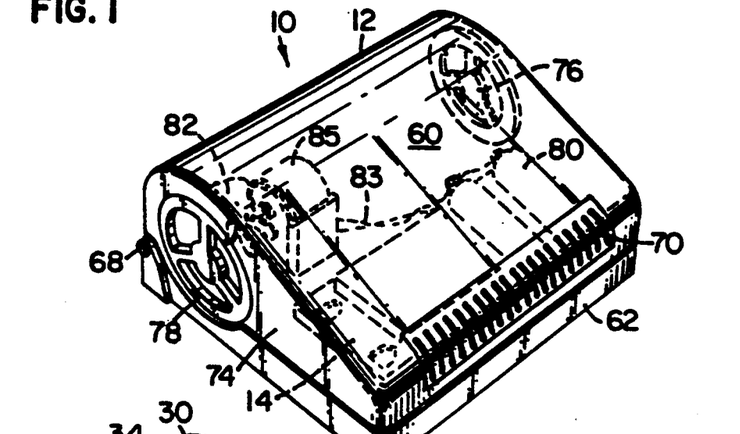
FIG. 1 is a perspective view of the air freshener device with dashed lines showing the inner workings of the present invention including the fragrance cartridge.
Figure 3:
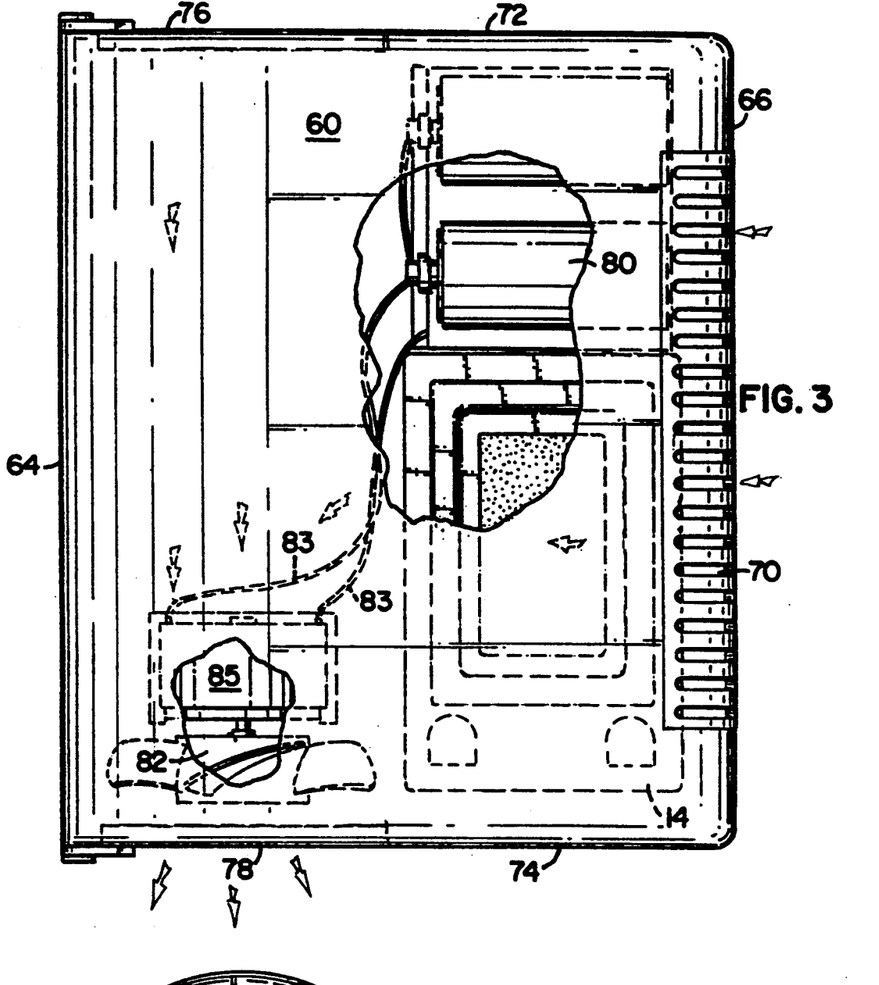
FIG. 3 is a top view of the device of FIG. 1 with break aways to show the fragrance cartridge, power means, and fan.
Figure 4:
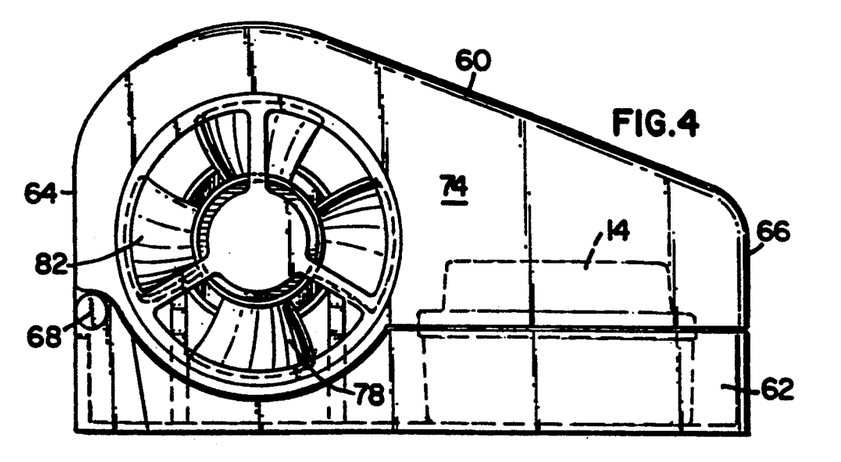
FIG. 4 is an end view of the device of FIG. 1.

Referring to FIGS. 1, 3 and 4, the outer housing 12, includes cover member 60 and a base member 62. The housing 12 is made of polycarbonate material such as Lexan ® in the preferred embodiment. It should be understood that other materials such as ABS plastic or Cycalac may be used. Cover member 60 has a first side 64 and a second side 66. In the preferred embodiment, a hinge 68 located proximate the first side 64 is used to pivotally secure cover member 60 to base member 62. This pivotal connection allows access to the inner workings of the device 10.

A first air passage opening 70 is located proximate the second side 66 of cover member 60. The first air passage opening 70 consists of a plurality of generally rectangular slots in the preferred embodiment. Cover member 60 also includes a top 72 and a bottom 74. The top 72 and bottom 74 respectively include second and third air passage openings 76 and 78. The air passage openings 76 and 78 are generally circular in cross section and are divided into three separate generally triangular portions in the preferred embodiment. It should be understood that other configurations of air passage openings may be utilized in the present invention.

Base member 62 is adapted and configured to be mounted on a surface. For example, the base member 62 may be mounted above a door so the user is exposed to the fragrance when entering a room. As shown in FIG. 3, base member 62 contains the fragrance cartridge 14. The cartridge 14 is placed such that small openings 56 are proximate the bottom 74 and the cartridge 14 is adjacent second side 66 of the cover member 60 in the preferred embodiment. Power means 80 are also connected to base member 62. In the preferred embodiment, the power means 80 are batteries, but it should be understood that any other suitable means to supply power may be utilized. The power means 80 supply power to a fan 82 by means of wires 83 which connect them. The power means 80 are positioned, proximate second side 66 and away from the air flow path between air passage openings 76 and 78. The fan 82 is positioned so as to be proximate the bottom 74 of cover member 60 and aligned with the air passage openings 76 and 78. The fan 82 is connected to the base member 62 in the preferred embodiment. The fan 82 includes a motor 85. In the preferred embodiment, the motor 85 is a 3 volt motor driven by two 1.5 volt batteries resulting in a fan having 600 rpm. However, it should be understood that any other placement of fan 82 or power means 80 which follows in the spirit of the present invention may be utilized.

After the user has removed the cover 37 to open the selected openings 34 and 54 exposing the fragrances 22 and 24 of cavities 18 and 20, the cartridge 14 is ready for use. As previously discussed, the size and number of openings 34 and 54 are predetermined. The removal of the cover 37 to open openings 34 and 54 to expose fragrances 22 and 24 allows control of the rate of evaporation, as well as the mixing of the fragrances 22 and 24.

The power means 80 powers the fan 82. The fan 82 creates an unobstructed air flow between the second and third air passage openings 76 and 78. The air enters the second air passage opening 76 and flows toward the third air passage opening 78 and then exits the third air passage opening 78. This air flow is not obstructed by the fragrance cartridge 14 or the power means 80. Air is also drawn into the device through the first air passage opening 70. This air moves over the fragrance cartridge 14 picking up fragrances 22 and 24. This air-fragrance mixture is drawn into the unobstructed air stream between the second and third air passage openings 76 and 78 by the low pressure created by the action of the fan 82. The air-fragrance flow is shown by arrows in FIG. 3. This side venting of the fragrances to the fan blade and the unobstructed flow allow dual air flow and allow the air-fragrance mixture to exit the device easily and to enter the environment at a greater velocity which aids in the dispersion of the mixture. The negative pressure created at the back of the fan 82 may create a turbulence which causes a portion of the air-fragrance mixture to exit the device 10 through the first air passage opening 70.

When the fragrance cartridge 14 has expired, it may be replaced by a refill cartridge which is identical to the fragrance cartridge 14. The refill cartridge is placed in the same position as the expired cartridge.

It should be understood that although the invention has been described as having a top, bottom and sides for purposes of clarity, any suitable orientation of the apparatus may be used.

Other modifications of the invention will be apparent to those skilled in the art in light of the foregoing description. This description is intended to provide specific examples of individual embodiments which clearly disclose the present invention. Accordingly, the invention is not limited to those embodiments for the use of elements having specific configurations and shapes as presented herein. All alternative modifications and variations of the present invention which follow in spirit and broad scope of the appended claims are included.

What is claimed is:

1. A cartridge for an air freshener device, comprising:
   (a) a housing, the housing have a sealed first cavity and a sealed second cavity;
   (b) a first fragrance located within the first cavity, the first fragrance having a first volatility;
   (c) a second fragrance located within the second cavity, the second fragrance having a second volatility;
   (d) the first cavity having a first opening therein, the first opening having a removable cover;
   (e) the second cavity having a second opening therein, the second opening having a removable cover; and
   (f) whereby when the covers are removed the fragrances of first and second volatilities independently exit their respective cavities.

2. The cartridge of claim 1 wherein the second cavity contains a greater volume of fragrance than the first cavity, the first fragrance having first volatility lower than the second volatility of the second fragrance.

3. The cartridge of claim 1 wherein the first cavity is sized and configured to generally rest on the second cavity, the second cavity sized and configured to support the first cavity.

4. The cartridge of claim 1 wherein the first opening is generally larger than the second opening, thereby allowing greater exposure of the fragrance of lower volatility and less exposure of the fragrance of higher volatility, whereby when the removable covers are removed the fragrances within the first and second cavities may independently exit their respective cavities thereby equalizing the rate of evaporation of the fragrances.

5. The cartridge of claim 1 wherein the second opening is sized, in relation to the first opening, so that the rates of evaporation of the first and second fragrances are controlled, thereby causing the fragrances to expire at approximately the same time.

6. The cartridge of claim 1 wherein the housing forms a single integral unit containing the first and second fragrances whereby when the covers are removed and the unit is inserted into an air freshener device, the unit allows independent exiting of the first and second fragrances.

7. The cartridge of claim 1, wherein the cover for the first opening is separate from the cover for the second opening.

8. A cartridge for an air freshener device, comprising:
(a) a housing having a sealed first cavity and a sealed cavity, the first cavity sized and configured to generally rest on the second cavity, the second cavity sized and configured to support the first cavity;
(b) a first fragrance located within the first cavity, the first fragrance having a first volatility;
(c) a second fragrance located within the second cavity, the second fragrance having a second volatility, wherein the second cavity contains a greater volume of fragrance than the first cavity, the first volatility lower than the second volatility;
(d) the first cavity having a first opening therein, the first opening having a removable cover;
(e) the second cavity having a second opening therein, the second opening having a removable cover, wherein the first opening is generally larger than the second opening, thereby allowing greater exposure of the fragrance of lower volatility and less exposure of the fragrance of higher volatility, whereby when the removable covers are removed, the fragrances within the first and second cavities may independently exit their respective cavities thereby equalizing the rate of evaporation of the fragrances.

9. The cartridge of claim 8 wherein the rates of evaporation of the first and second fragrances are controlled, thereby causing the fragrances to expire at approximately the same time.

10. The cartridge of claim 8 wherein the housing forms a single integral unit containing the first and second fragrances whereby when the cover is removed and the unit is inserted into the air freshener device the unit allows independent exiting of the first and second fragrances.

11. The cartridge of claim 8, wherein the cover for the first opening is separate from the cover for the second opening.

* * * * *